United States Patent
Ishikura et al.

(10) Patent No.: US 8,361,493 B2
(45) Date of Patent: *Jan. 29, 2013

(54) TRANSDERMAL PATCH HAVING A PRESSURE-SENSITIVE ADHESIVE COMPRISING (METH)ACRYLIC ACID ALKYL ESTER, N-HYDROXYALKYL(METH)ACRYLAMIDE, AND VINYL MONOMERS

(75) Inventors: Jun Ishikura, Ibaraki (JP); Raito Funayama, Ibaraki (JP); Yu Tachikawa, Ibaraki (JP); Junichi Sekiya, Ibaraki (JP); Tsuyoshi Kasahara, Ibaraki (JP); Ryo Hashino, Ibaraki (JP); Satoshi Ameyama, Ibaraki (JP); Hidetoshi Kuroda, Ibaraki (JP)

(73) Assignee: Nitto Denko Corporation, Ibaraki-shi (JP)

( * ) Notice: Subject to any disclaimer, the term of this patent is extended or adjusted under 35 U.S.C. 154(b) by 14 days.

This patent is subject to a terminal disclaimer.

(21) Appl. No.: 12/945,198

(22) Filed: Nov. 12, 2010

(65) Prior Publication Data

US 2011/0123598 A1    May 26, 2011

(30) Foreign Application Priority Data

Nov. 20, 2009 (JP) ................................. 2009-265713

(51) Int. Cl.
*A61F 13/02* (2006.01)
*A61F 13/00* (2006.01)

(52) U.S. Cl. .................... 424/448; 424/449; 428/355

(58) Field of Classification Search .................... None
See application file for complete search history.

(56) References Cited

U.S. PATENT DOCUMENTS

| 5,288,827 | A | * | 2/1994 | Li et al. .......................... 526/279 |
| 6,146,656 | A | * | 11/2000 | Hori et al. ..................... 424/448 |
| 6,465,004 | B1 | * | 10/2002 | Rossi-Montero et al. .... 424/448 |
| 2010/0215947 | A1 | * | 8/2010 | Yamanaka et al. ............ 428/323 |

FOREIGN PATENT DOCUMENTS

| JP | 4-150865 | 5/1992 |
| JP | 2003-313122 | 11/2003 |
| WO | WO 2009/054106 | * 4/2009 |

OTHER PUBLICATIONS

U.S. Appl. No. 13/399,384, filed Feb. 17, 2012, Hashino, et al.

* cited by examiner

*Primary Examiner* — Kevin S Orwig
(74) *Attorney, Agent, or Firm* — Oblon, Spivak, McClelland, Maier & Neustadt, L.L.P.

(57) ABSTRACT

The patch according to an embodiment of the present invention includes: a support; and a pressure-sensitive adhesive layer on at least one surface of the support, wherein: the pressure-sensitive adhesive layer contains an acrylic copolymer obtained by copolymerizing monomer components containing (a) at least one kind of a monomer of a (meth)acrylic acid alkyl ester and (b) at least one kind of a monomer of an N-hydroxyalkyl(meth)acrylamide; a content of the (meth)acrylic acid alkyl ester monomer (a) with respect to a total amount of the monomer components is 50 wt % to 90 wt % and a content of the N-hydroxyalkyl(meth)acrylamide monomer (b) with respect to the total amount is 1 wt % to 20 wt %; and the monomer components are substantially free of a monomer having a carboxyl group.

12 Claims, 1 Drawing Sheet

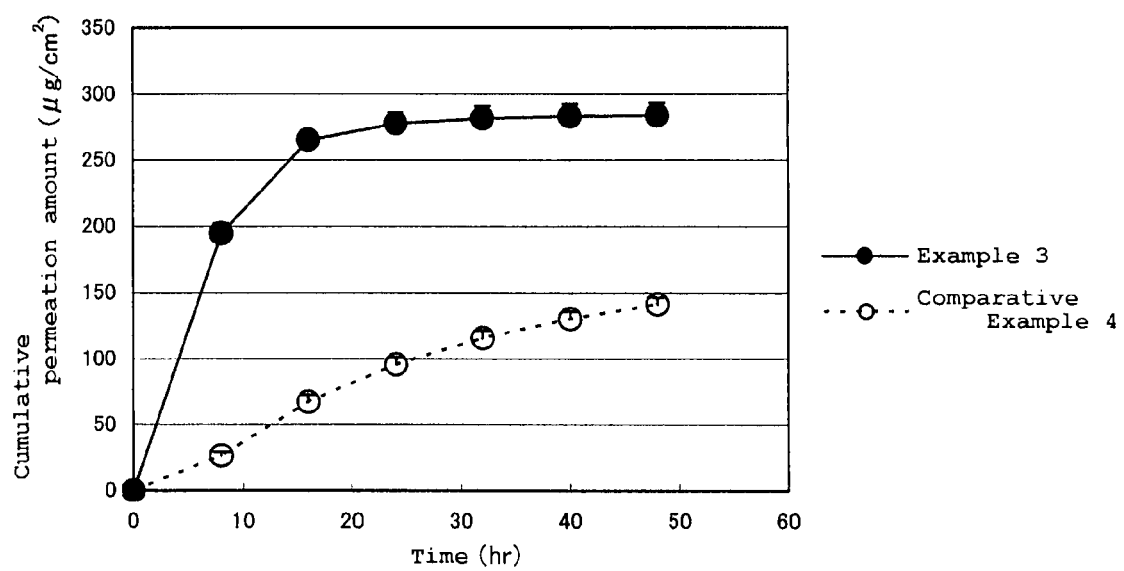

TRANSDERMAL PATCH HAVING A PRESSURE-SENSITIVE ADHESIVE COMPRISING (METH)ACRYLIC ACID ALKYL ESTER, N-HYDROXYALKYL(METH)ACRYLAMIDE, AND VINYL MONOMERS

This application claims priority under 35 U.S.C. Section 119 to Japanese Patent Application No. 2009-265713 filed on Nov. 20, 2009, which are herein incorporated by references.

BACKGROUND OF THE INVENTION

1. Field of the Invention

The present invention relates to a patch and a patch preparation each of which is used for the protection of a skin, the transdermal administration of a drug, and the like.

2. Description of the Related Art

Patches and patch preparations each of which is used by being attached to a skin for the purposes of, for example, protecting the skin, fixing various medical devices, and transdermally administering a drug are each requested to have the following characteristics. That is, each of the patches and patch preparations shows sufficient pressure-sensitive adhesiveness upon attachment to the skin, and can be released and removed without contaminating the surface of the skin (causing, for example, an adhesive residue or stickiness) after its use. In addition, it is desirable that each of the patches and patch preparations be lowly stimulant to the skin.

Japanese Laid-open Patent Publication No. Hei 4-150865 discloses a patch containing, in its pressure-sensitive adhesive layer, a cross-linked product of a copolymer of: a (meth) acrylic acid alkyl ester or a mixture of the ester and a (meth) acrylic acid alkoxyalkyl ester; and a monomer containing a carboxyl group and/or a hydroxyl group. However, reactivity between an active component such as a drug and a carboxyl group must be taken into consideration because the pressure-sensitive adhesive layer in the above-mentioned patch contains the copolymer having a carboxyl group.

In addition, Japanese Laid-open Patent Publication No. 2003-313122 discloses a patch using an acrylic pressure-sensitive adhesive obtained by polymerizing: (meth)acrylic acid alkyl esters; and monomers copolymerizable with the (meth) acrylic acid alkyl ester and free of a carboxyl group and a sulfo group. Further, the pressure-sensitive adhesive layer of the patch in the document contains an organic liquid component and can be cross-linked. The document describes that the above-mentioned patch shows a small stimulus to a skin and has a feeling of softness while having such a sufficient cohesive strength that no adhesive residue occurs at the time of its release. However, an additional improvement in adhesive property of the pressure-sensitive adhesive free of a carboxyl group and a sulfo group disclosed in Japanese Laid-open Patent Publication No. 2003-313122 has been desired because the patch may be released from the skin when the patch is attached to a skin surface for a long time period or attached to a skin surface that moves to a large extent.

SUMMARY OF THE INVENTION

In view of the foregoing, an object of the present invention is to provide a patch or patch preparation having the following characteristics:

(A) even when a drug or the like is incorporated into a pressure-sensitive adhesive layer, denaturation or the like due to a reaction with such component can be suppressed;

(B) the patch or patch preparation has a sufficient cohesive strength and causes no adhesive residue at the time of release;

(C) the patch or patch preparation shows good adhesion for a skin, but shows a small stimulus to the skin and has a soft feeling of attachment; and (D) the patch or patch preparation is particularly suitable for the purposes of, for example, protecting the skin and transdermally administering the drug.

The inventors of the present invention have made extensive studies to solve the above-mentioned problems. As a result, the inventors have found that the use of a pressure-sensitive adhesive containing an acrylic copolymer obtained by copolymerizing the following monomer components as a composition for forming the pressure-sensitive adhesive layer of a patch or the like provides a patch or the like that satisfies all of the above-mentioned characteristics (A) to (D). That is, the monomer components contain one or two or more kinds of monomers of (meth)acrylic acid alkyl esters and one or two or more kinds of monomers of N-hydroxyalkyl(meth)acrylamides, and are substantially free of a monomer having a carboxyl group.

A patch according to an embodiment of the present invention includes: a support; and a pressure-sensitive adhesive layer on at least one surface of the support, wherein: the pressure-sensitive adhesive layer contains an acrylic copolymer obtained by copolymerizing monomer components containing (a) at least one kind of a monomer of a (meth)acrylic acid alkyl ester and (b) at least one kind of a monomer of an N-hydroxyalkyl(meth)acrylamide; a content of the (meth) acrylic acid alkyl ester monomer (a) with respect to a total amount of the monomer components is 50 wt % to 90 wt % and a content of the N-hydroxyalkyl(meth)acrylamide monomer (b) with respect to the total amount is 1 wt % to 20 wt %; and the monomer components are substantially free of a monomer having a carboxyl group.

In a preferred embodiment of the invention, the acrylic copolymer is obtained by copolymerizing the monomer components further containing (c) a vinyl-based monomer.

In a preferred embodiment of the invention, a content of the vinyl-based monomer (c) is 1 wt % to 40 wt % with respect to the total amount of the monomer components.

In a preferred embodiment of the invention, the pressure-sensitive adhesive layer further includes an organic liquid component.

In a preferred embodiment of the invention, the pressure-sensitive adhesive layer is cross-linked.

According to another aspect of the present invention, a patch preparation is provided. The patch preparation obtained by incorporating a drug that can be transdermally administered into the pressure-sensitive adhesive layer in the patch according to the patch.

When an active component such as a drug is incorporated into the pressure-sensitive adhesive layer of each of the patch and patch preparation of the present invention, the denaturation of the above-mentioned active component, the inhibition of the movement of the above-mentioned active component in the pressure-sensitive adhesive layer, and the like caused by a reaction between the above-mentioned active component and a functional group in the pressure-sensitive adhesive layer can be suppressed. In addition, each of the patch and patch preparation of the present invention has a sufficient cohesive strength, causes no adhesive residue at the time of release, and shows good adhesion for a skin, but shows a small stimulus to the skin and has a soft feeling of attachment. Therefore, the patch and the patch preparation are particularly suitable as a patch for use in, for example, the protection of the skin and a patch preparation for use in the transdermal administration of the drug, respectively.

BRIEF DESCRIPTION OF THE DRAWINGS

FIG. 1 is a graph illustrating the skin permeability of pramipexole for each of patch preparations of Example 3 and Comparative Example 4 of the present invention.

DETAILED DESCRIPTION OF THE PREFERRED EMBODIMENTS

A patch of the present invention includes a pressure-sensitive adhesive layer on at least one surface of a support, in which the pressure-sensitive adhesive layer includes a pressure-sensitive adhesive that contains an acrylic copolymer obtained by copolymerizing monomer components containing (a) one or two or more kinds of monomers of (meth) acrylic acid alkyl esters and (b) one or two or more kinds of monomers of N-hydroxyalkyl(meth) acrylamides.

The above-mentioned (meth) acrylic acid alkyl esters (monomers (a)) are typically represented by the following formula (I).

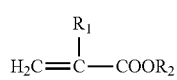
(I)

In the formula, $R_1$ represents a hydrogen atom or a methyl group, and $R_2$ represents an alkyl group. The alkyl group is preferably an alkyl group having 4 to 18 carbon atoms. In order that good adhesion (tack) enough for use in a patch or the like may be obtained, a pressure-sensitive adhesive having a low glass transition temperature must be obtained. When the alkyl group has 4 to 18 carbon atoms, a pressure-sensitive adhesive having a sufficiently low glass transition temperature is easily obtained.

Examples of the above-mentioned (meth)acrylic acid alkyl esters include those each having: a straight-chain alkyl group such as n-butyl, n-pentyl, n-hexyl, n-heptyl, n-octyl, n-nonyl, n-decyl, n-undecyl, n-dodecyl, or n-tridecyl; a branched-chain alkyl group such as isobutyl, isopentyl, isohexyl, isooctyl, or 2-ethylhexyl; or a cyclic alkyl group such as cyclopentyl, cyclohexyl, or cycloheptyl. They may be used alone or in combination.

Of the above-mentioned esters, a monomer component that reduces a glass transition temperature is preferably used in order that pressure-sensitive adhesiveness may be imparted at normal temperature. A (meth)acrylic acid alkyl ester in which the alkyl group represented by $R_2$ in the formula (I) has 4 to 12 carbon atoms is more preferred. To be specific, butyl acrylate, butyl methacrylate, 2-ethylhexyl acrylate, 2-ethylhexyl methacrylate, cyclohexyl acrylate, cyclohexyl methacrylate, or the like is preferred, and 2-ethylhexyl acrylate is most preferred. This is because of the following reasons. That is, a polymer having a sufficiently low glass transition temperature (−70° C.) is obtained when the ester is polymerized. In addition, the ester is easily available.

The above-mentioned monomers (a) used in the present invention are preferably selected so that a homopolymer composed of the monomers may have a glass transition temperature of preferably −80° C. to −40° C. and particularly preferably −70° C. to −50° C.

The content of the above-mentioned monomers (a) is 50 wt % or more with respect to the total amount of the monomer components. When the content of the monomers (a) is 50 wt % or more, adhesion (tack) upon use as a pressure-sensitive adhesive is good. In addition, the content of the monomers (a) is preferably 60 wt % or more in order that additionally good tack may be obtained. On the other hand, when the content of the monomers (a) in the above-mentioned monomer components is excessively large, the properties of the resultant copolymer are close to those of the homopolymer of the monomers (a) described above, and hence properties proper for a pressure-sensitive adhesive tend to be hardly obtained. Therefore, the content of the monomers (a) is 90 wt % or less, preferably 80 wt % or less, and more preferably 75 wt % or less with respect to the total amount of the monomer components.

The N-hydroxyalkyl(meth)acrylamides (monomers (b)) are typically represented by the following formula (II).

(II)

In the formula, $R_3$ represents a hydrogen atom or a methyl group, and $R_4$ represents a hydroxyalkyl group.

As the above-mentioned hydroxyalkyl group in the formula (II), a hydroxyalkyl group having 2 to 4 carbon atoms is preferred. The alkyl group in the above-mentioned hydroxyalkyl group may be linear or branched. Examples of the N-hydroxyalkyl(meth)acrylamide represented by the formula (II) include N-(2-hydroxyethyl)acrylamide, N-(2-hydroxyethyl)methacrylamide, N-(2-hydroxypropyl)acrylamide, N-(2-hydroxypropyl)methacrylamide, N-(1-hydroxypropyl)acrylamide, N-(1-hydroxypropyl)methacrylamide, N-(3-hydroxypropyl)acrylamide, N-(3-hydroxypropyl)methacrylamide, N-(2-hydroxybutyl)acrylamide, N-(2-hydroxybutyl)methacrylamide, N-(3-hydroxybutyl)acrylamide, N-(3-hydroxybutyl)methacrylamide, N-(4-hydroxybutyl)acrylamide, and N-(4-hydroxybutyl)methacrylamide. They may be used alone or in combination. Preferred examples of the monomers (b) in the present invention include N-(2-hydroxyethyl)acrylamide and N-(2-hydroxyethyl)methacrylamide. A particularly preferred example of the monomers (b) is N-(2-hydroxyethyl)acrylamide (HEAA). This is because it is possible to form a pressure-sensitive adhesive layer having good hydrophilic and hydrophobic balance and having excellent pressure-sensitive adhesiveness balance. For example, HEAA accounts for preferably 50 wt % or more, more preferably 70 wt % or more, still more preferably substantially all of the monomers (b).

The monomers (b) can contribute to an improvement in cohesiveness of a pressure-sensitive adhesive by virtue of an interaction between their molecules. In the present invention, the content of the monomers (b) is 1 wt % to 20 wt % with respect to the total amount of the monomer components. When the content of the monomers (b) is 1 wt % or more, a sufficient cohesive strength can be imparted to the pressure-sensitive adhesive, and hence the following risks can be avoided. That is, an adhesive lies off an end face of a patch toward the outside owing to the movement of a skin to cause the contamination of a garment or the like, or an adhesive residue occurs on the skin at the time of the release of the patch. On the other hand, when the content of the monomers (b) exceeds 20 wt %, tack may reduce to cause, for example, the floating, or the release of an end, of the patch in the case of an adherend having a rough surface and stretching property such as a skin.

In a preferred embodiment of the present invention, the content of the monomers (b) is 2 wt % to 20 wt %, more preferably 3 wt % to 15 wt %, still more preferably 3 wt % to 12 wt % with respect to the total amount of the monomer components. With a pressure-sensitive adhesive containing an acrylic copolymer obtained by copolymerizing the monomer components containing the monomers (b) at such ratio, even in, for example, the case where the monomer components subjected to copolymerization are substantially free of a monomer having a heteroatom other than oxygen (such as nitrogen or sulfur) except the monomers (b), a cohesive strength and an adhesive strength when the composition is bonded to a skin surface can be additionally improved. The phrase "substantially free of a monomer having a heteroatom" as used in the specification comprehends not only the case where the content of the monomer having a heteroatom is zero but also the case where the content is 0.1 wt % or less with respect to the total amount of the monomer components.

A weight ratio (a:b) between the monomers (a) and (b) in the monomer components is, for example, 99.9:0.1 to 71:29, preferably 99:1 to 75:25, more preferably 98:2 to 80:20, still more preferably 97:3 to 85:15. As long as the weight ratio (a:b) falls within such range, a patch or the like having an additionally good cohesive strength and an additionally good adhesive strength when bonded to a skin surface can be obtained even in, for example, the case where the monomer components subjected to copolymerization are of such composition as to be substantially free of a monomer having a heteroatom other than oxygen (such as nitrogen or sulfur) except the monomers (b) (e.g., the monomer components are substantially composed of the monomers (a) and (b)).

The total content of the monomers (a) and (b) is preferably about 60 wt % or more, more preferably about 80 wt % or more, still more preferably about 90 wt % or more, particularly preferably about 95 wt % or more with respect to the total amount of the monomer components. In a preferred embodiment of the present invention, pressure-sensitive adhesive for forming the pressure-sensitive adhesive layer includes acrylic copolymer obtained by substantially copolymerizing only the monomers (a) and (b) (that is, the total content of the monomers (a) and (b) substantially accounts for 100 wt % of all the monomer components). With such pressure-sensitive adhesive, a patch having a good cohesive strength and a good adhesive strength when bonded to a skin surface can be obtained, even though the pressure-sensitive adhesive is composed by simple composition.

In the present invention, the above-mentioned monomer components subjected to copolymerization are characterized by being substantially free of a monomer having a carboxyl group. The term "monomer having a carboxyl group" as used herein typically refers to, for example, an ethylenically unsaturated monomer having at least one carboxyl group in its molecule (the carboxyl group may be in a form of an anhydride) (typically a vinyl-based monomer). Examples of such monomer having a carboxyl group include: ethylenically unsaturated monocarboxylic acids such as (meth)acrylic acid and crotonic acid; ethylenically unsaturated dicarboxylic acids such as maleic acid, itaconic acid, and citraconic acid; and anhydrides of ethylenically unsaturated dicarboxylic acids such as maleic anhydride and itaconic anhydride. It should be noted that the phrase "the monomer components are substantially free of a monomer having a carboxyl group" as used in the specification comprehends not only the case where the monomer components subjected to copolymerization are completely free of the monomer having a carboxyl group but also the case where the content of the monomer is 0.1 wt % or less with respect to the total amount of the monomer components.

Further, in the present invention, it is preferred that the above-mentioned monomer components subjected to copolymerization not only be substantially free of a monomer having a carboxyl group but also be substantially free of a monomer having an acidic group other than a carboxyl group (such as a sulfo group or a phosphate group). That is, it is preferred that the above-mentioned monomer components be completely free of the monomer having a carboxyl group and the monomer having any other acidic group or contain these monomers at a content of 0.1 wt % or less with respect to their total amount. The incorporation of a medical active component such as a drug into a pressure-sensitive adhesive layer formed by using a pressure-sensitive adhesive containing a copolymer obtained by copolymerizing the above-mentioned monomers can forestall, for example, the denaturation of the above-mentioned active component and the inhibition of the movement of the active component in the pressure-sensitive adhesive layer due to a reaction with the above-mentioned carboxyl group or the like.

In the present invention, a vinyl-based monomer (c) copolymerizable with the above-mentioned monomers (a) and (b) as well as these monomers can be incorporated into the above-mentioned monomer components for composing the acrylic copolymer. The addition of the monomer (c) can adjust: the pressure-sensitive adhesive strength and cohesive strength of each of the patch and the patch preparation; and the solubility and discharge property of a drug.

When the monomer (c) is incorporated into the monomer components subjected to copolymerization in the present invention, its content is preferably 40 wt % or less, more preferably 1 wt % to 40 wt %, still more preferably 1 wt % to 35 wt %, particularly preferably 5 wt % to 30 wt % with respect to the total amount of the monomer components. When the content of the monomer (c) is 1 wt % or more, an effect of the incorporation of the monomer (c) is sufficiently exerted. In addition, when the content of the monomer (c) exceeds 40 wt %, the tack or pressure-sensitive adhesive strength of each of the resultant patch and patch preparation may reduce.

Vinyl ethers such as methyl vinyl ether and ethyl vinyl ether, and vinyl-based monomers each having a heterocycle containing a nitrogen atom such as N-vinyl-2-pyrrolidone, 1-vinyl caprolactam, 2-vinyl-2-piperidone, and 1-vinylimidazole can each be used as the vinyl-based monomer (c). They may be used alone or in combination. It should be noted that a vinyl-based monomer having a heterocycle containing a nitrogen atom among the above-mentioned vinyl-based monomers is preferably used.

In the present invention, a polymerization method for obtaining the acrylic copolymer from the above-mentioned monomer components is not particularly limited, and any appropriate polymerization method can be adopted. For example, a polymerization method involving the use of a thermal polymerization initiator (a thermal polymerization method such as a solution polymerization method, an emulsion polymerization method, or a bulk polymerization method), or a polymerization method involving applying an active energy ray (also referred to as "high-energy ray") such as light or radiation can be adopted.

Of the above-mentioned polymerization methods, the solution polymerization method can be preferably adopted because the method is excellent in, for example, workability and quality stability. The mode of the solution polymerization is not particularly limited, and any appropriate mode can be adopted. To be specific, any appropriate monomer supply method, polymerization conditions (such as a polymerization temperature, a polymerization time, and a polymerization pressure), and materials to be used (such as a polymerization initiator and a surfactant) can be adopted. Any one of, for example, a batch loading system involving supplying the total amount of the monomer components to a reaction vessel in one stroke, a continuous supply (dropping) system, and a split supply (dropping) system can be adopted as the above-mentioned monomer supply method. A preferred mode is, for example, such a mode that a solution prepared by dissolving the total amount of the monomer components and an initiator in a solvent is supplied to the reaction vessel and then the monomer components are collectively polymerized (batch polymerization). Such batch polymerization is preferred because a polymerization operation and process control are easy. Another preferred mode is, for example, such a mode that an initiator (typically a solution prepared by dissolving the initiator in a solvent) is prepared in a reaction vessel and then a solution prepared by dissolving the monomer components in a solvent is polymerized while being dropped into the reaction vessel (dropping polymerization or continuous polymerization). Part of the monomer components (part of the components and/or part of the amount) may be loaded into the reaction vessel typically together with a solvent, and the remaining monomer components may be dropped into the reaction vessel. When the monomer components containing the monomers (b) at a content of 15 wt % or more are polymerized, the dropping polymerization is more preferably employed from the viewpoint of the ease with which a polymerization reaction is uniformly advanced.

Examples of the above-mentioned thermal polymerization initiator include: azo-based compounds (azo-based initiators) such as 2,2'-azobisisobutyronitrile, 2,2'-azobis-2-methylbutyronitrile, dimethyl 2,2'-azobis(2-methylpropionate), 4,4'-azobis-4-cyanovaleric acid, azobisisovaleronitrile, 2,2'-azobis(2-amidinopropane) dihydrochloride, 2,2'-azobis[2-(5-methyl-2-imidazolin-2-yl)propane]dihydrochloride, 2,2'-azobis(2-methylpropionamidine) disulfate, 2,2'-azobis(N,N'-dimethyleneisobutylamidine) dihydrochloride, and 2,2'-azobis[N-(2-carboxyethyl)-2-methylpropionamidine] hydrate; persulfates such as potassium persulfate and ammonium persulfate; peroxides (peroxide-based initiators) such as dibenzoyl peroxide, tert-butyl permaleate, t-butyl hydroperoxide, and hydrogen peroxide; substituted ethane-based initiators such as phenyl-substituted ethane; and redox-type initiators such as a mixed agent of a persulfate and sodium hydrogen sulfite, and a mixed agent of a peroxide and sodium ascorbate. When monomer components are polymerized by a thermopolymerization method, the polymerization temperature is preferably about 20° C. to about 100° C., more preferably about 40° C. to about 80° C.

A polymerization method involving applying light (typically UV light) is typically performed by using a photopolymerization initiator. The photopolymerization initiator is not particularly limited, and for example, a ketal-based photopolymerization initiator, an acetophenone-based photopolymerization initiator, a benzoin ether-based photopolymerization initiator, an acylphosphine oxide-based photopolymerization initiator, an α-ketol-based photopolymerization initiator, an aromatic sulfonyl chloride-based photopolymerization initiator, an optically active oxime-based photopolymerization initiator, a benzoin-based photopolymerization initiator, a benzyl-based photopolymerization initiator, a benzophenone-based photopolymerization initiator, or a thioxanthone-based photopolymerization initiator can be used. Such photopolymerization initiators may be used alone or in combination.

Examples of the ketal-based photopolymerization initiator include 2,2-dimethoxy-1,2-diphenylethan-1-one [such as one under the trade name "Irgacure 651" (manufactured by Ciba Japan KK)]. Examples of the acetophenone-based photopolymerization initiator include 1-hydroxycyclohexyl phenyl ketone [such as one under the trade name "Irgacure 184" (manufactured by Ciba Japan KK)], 2,2-diethoxyacetophenone, 2,2-dimethoxy-2-phenylacetophenone, 4-phenoxydichloroacetophenone, and 4-(t-butyl) dichloroacetophenone. Examples of the benzoin ether-based photopolymerization initiator include benzoin methyl ether, benzoin ethyl ether, benzoin propyl ether, benzoin isopropyl ether, and benzoin isobutyl ether. Examples of the acylphosphine oxide-based photopolymerization initiator include one under the trade name "Lucirin TPO" (manufactured by BASF). Examples of the α-ketol-based photopolymerization initiator include 2-methyl-2-hydroxypropiophenone and 1-[4-(2-hydroxyethyl)phenyl]-2-methylpropan-1-one.

Examples of the aromatic sulfonyl chloride-based photopolymerization initiator include 2-naphthalenesulfonyl chloride. Examples of the optically active oxime-based photopolymerization initiator include 1-phenyl-1,1-propanedione-2-(o-ethoxycarbonyl)-oxime. Examples of the benzoin-based photopolymerization initiator include benzoin. Examples of the benzyl-based photopolymerization initiator include benzyl. Examples of the benzophenone-based photopolymerization initiator include benzophenone, benzoylbenzoic acid, 3,3'-dimethyl-4-methoxybenzophenone, polyvinylbenzophenone, and α-hydroxycyclohexyl phenyl ketone. Examples of the thioxanthone-based photopolymerization initiator include thioxanthone, 2-chlorothioxanthone, 2-methylthioxanthone, 2,4-dimethylthioxanthone, isopropylthioxanthone, 2,4-diisopropylthioxanthone, and dodecylthioxanthone.

The usage of the above-mentioned polymerization initiator is not particularly limited. For example, the usage of the polymerization initiator is preferably about 0.01 part by weight to about 2 parts by weight, more preferably about 0.01 part by weight to about 1 part by weight with respect to 100 parts by weight of the total amount of the monomer components.

In the present invention, the patch is produced as described below. That is, a composition containing the above-mentioned acrylic copolymer (which may hereinafter be referred to as "composition for forming a pressure-sensitive adhesive layer" or "pressure-sensitive adhesive") is formed into the pressure-sensitive adhesive layer on at least one surface of the support.

In the present invention, the composition for forming the pressure-sensitive adhesive layer containing the acrylic copolymer described above may be subjected to a physical cross-linking treatment based on, for example, the application of radiation such as the application of UV light or the application of an electron beam, or to a chemical cross-linking treatment with any one of various cross-linking agents as desired. Any appropriate cross-linking agent can be appropriately selected as one of the above-mentioned cross-linking agents. For example, an isocyanate-based compound (isocyanate-based cross-linking agent), an epoxy-based cross-linking agent, an aziridine-based cross-linking agent, a melamine-based cross-linking agent, a peroxide-based cross-linking agent, an oxazoline-based cross-linking agent, a urea-based cross-linking agent, an amino-based cross-linking agent, a carbodiimide-based cross-linking agent, or a coupling agent-based cross-linking agent (such as a silane coupling agent) can be used. They may be used alone or in combination. The use of any such cross-linking agent to cross-link (cure) the pressure-sensitive adhesive layer can not only impart a moderate cohesive strength and a moderate pressure-sensitive adhesive strength to the pressure-sensitive adhesive layer but also reduce an adhesive residue at the time of the release of the pressure-sensitive adhesive layer from a skin. In the present invention, the cross-linking agent used for cross-linking the pressure-sensitive adhesive layer is added at a content of preferably about 0.01 part by weight to about 5 parts by weight, more preferably about 0.01 part by weight to about 2 parts by weight with respect to 100 parts by weight of the acrylic copolymer.

The pressure-sensitive adhesive layer cross-linked with the above-mentioned cross-linking agent has a gel fraction of preferably 50 wt % to 95 wt %, more preferably 60 wt % to 92 wt %. When the gel fraction of the pressure-sensitive adhesive layer is 50 wt % to 95 wt %, a sufficient cohesive strength is imparted to the pressure-sensitive adhesive layer, and there is no possibility that an adhesive residue or a strong skin stimulus resulting from a cohesive failure arises at the time of the release of the patch. It should be noted that, when the gel fraction of the pressure-sensitive adhesive layer exceeds 95 wt %, the cohesive strength of the pressure-sensitive adhesive layer increases but a sufficient skin pressure-sensitive adhesive strength may not be obtained.

It should be noted that the above-mentioned term "gel fraction" refers to a ratio of the weight of insoluble matter obtained when the pressure-sensitive adhesive layer is immersed in an organic solvent such as ethyl acetate to the total weight of components involved in the cross-linking of the pressure-sensitive adhesive layer. The gel fraction can be determined from the weight of the insoluble matter obtained by immersing the pressure-sensitive adhesive layer in the organic solvent such as ethyl acetate at normal temperature (23° C.) for a predetermined time period by using the following equation:

$$\text{Gel fraction (wt \%)} = (W_2 \times 100)/(W_1 \times A/B)$$

where A represents the weight of the polymer and the cross-linking agent, B represents the total weight of the constituent components of the pressure-sensitive adhesive layer, $W_1$ represents the weight of the pressure-sensitive adhesive layer as a sample, and $W_2$ represents the weight of the insoluble matter obtained by immersing the pressure-sensitive adhesive layer as a sample in the organic solvent.

The composition for forming the pressure-sensitive adhesive layer in the patch of the present invention can further contain an organic liquid component having compatibility with the above-mentioned acrylic copolymer. The organic liquid component can plasticize the pressure-sensitive adhesive layer to provide a feeling of softness. As a result, when a pressure-sensitive adhesive containing the above-mentioned acrylic copolymer is used as a pressure-sensitive adhesive layer, pain or skin irritation resulting from a skin adhesive strength can be reduced upon release of a patch or patch preparation such as a pressure-sensitive adhesive tape or a transdermally absorbable preparation from a skin. Therefore, any component can be used as the organic liquid component without any particular limitation as long as the component has a plasticizing action. It should be noted that a component having an absorption-promoting action is preferably used for improving transdermal absorption property when a drug is incorporated into the pressure-sensitive adhesive layer.

Examples of the above-mentioned organic liquid component include: plant fats and oils such as olive oil, castor oil, and palm oil; animal fats and oils such as lanolin; organic solvents such as dimethyl decyl sulfoxide, methyl octyl sulfoxide, dimethyl sulfoxide, dimethylformamide, dimethylacetamide, dimethyllaurylamide, methylpyrrolidone, and dodecylpyrrolidone; liquid surfactants such as a polyoxyethylene sorbitan fatty acid ester, a sorbitan fatty acid ester, and a polyoxyethylene fatty acid ester; plasticizers such as diisopropyl adipate, a phthalate, and diethyl sebacate; hydrocarbons such as squalane and liquid paraffin; fatty acid alkyl esters such as ethyl oleate, isopropyl palmitate, octyl palmitate, isopropyl myristate, isotridecyl myristate, and ethyl laurate; fatty acid esters of polyhydric alcohols such as a glycerin fatty acid ester and a propylene glycol fatty acid ester; ethoxylated stearyl alcohol; and a pyrrolidone carboxylic acid fatty acid ester. They may be used alone or in combination.

In the present invention, the above-mentioned organic liquid component can be preferably incorporated into the acrylic copolymer at a weight ratio "acrylic copolymer:organic liquid component" of 1:0.1 to 2. The weight ratio is more preferably 1:0.4 to 2 from the viewpoint of skin stimulus property. It should be noted that the organic liquid component is preferably incorporated in as large an amount as possible to such an extent that pressure-sensitive adhesive properties are not impaired.

In addition, the composition of the present invention for forming the pressure-sensitive adhesive layer may further contain any other components as far as the features of the present invention are not impaired. Examples of such components include antioxidants such as ascorbic acid, tocopherol acetate, natural vitamin E, dibutylhydroxytoluene, and butylhydroxyanisole; amine-ketone-based anti-aging agents such as 2,6-tert-butyl-4-methylphenol; aromatic secondary amine-based anti-aging agents such as N,N'-di-2-naphthyl-p-phenylenediamine; monophenol-based anti-aging agents such as a 2,2,4-trimethyl-1,2-dihydroquinoline polymer; bisphenol-based anti-aging agents such as 2,2'-methylenebis (4-ethyl-6-tert-butylphenol); polyphenol-based anti-aging agents such as 2,5-tert-butylhydroquinone; fillers such as kaolin, hydrous silicon dioxide, zinc oxide, and starch acrylate 1000; softening agents such as propylene glycol, polybutene, and macrogol 1500; antiseptics such as benzoic acid, sodium benzoate, chlorhexidine hydrochloride, sorbic acid, methyl paraoxybenzoate, and butyl paraoxybenzoate; coloring agents such as yellow iron oxide, yellow iron(III) oxide, iron(III) oxide, black iron oxide, carbon black, carmine, β-carotene, copper chlorophyll, Food Blue No. 1, Food Yellow No 0.4, Food Red No. 2, and licorice extract; cooling agents such as fennel oil, d-camphor, dl-camphor, mint oil, d-borneol, and l-menthol; and perfumes such as spearmint oil, clove oil, vanillin, bergamot oil, and lavender oil.

In the present invention, the patch is obtained by forming the pressure-sensitive adhesive containing the acrylic copolymer into the pressure-sensitive adhesive layer on at least one surface of the support. The patch of the present invention can be provided as, for example, a sheet-, film-, or pad-shaped, medical or sanitary patch, and can find use in applications such as the protection of a lesion site or wounded site of a skin including an alternative to a gauze in a plaster and an alternative to a nonwoven fabric in a wound-covering dressing. In addition, the patch of the present invention can be turned into a patch preparation by incorporating a drug into its pressure-sensitive adhesive layer. The patch preparation of the present invention is provided as a transdermally absorbable preparation such as a matrix-type patch preparation, and a reservoir-type patch preparation, and is particularly provided as a tape drug for transdermal absorption. It should be noted that the above-mentioned pressure-sensitive adhesive layer is not limited to a continuously formed layer and may be a pressure-sensitive adhesive layer formed so as to be of a regular or random pattern such as a dot shape or a stripe shape.

The support used in each of the patch and patch preparation of the present invention is not particularly limited. The support is preferably constituted of such a material that a reduction in content of a component in the pressure-sensitive adhesive layer (e.g., an active component such as a drug, or an additive) does not occur owing to the loss of the component from the back surface of the support as a result of its permeation through the support. That is, the support is preferably constituted of a material that does not allow the permeation of the component in the pressure-sensitive adhesive layer.

Examples of the support used in each of the patch and the patch preparation include: polyester resins such as polyethylene terephthalate; polyamide-based resins such as nylon; olefin-based resins such as Saran (registered trade mark), polyethylene, polypropylene, and Surlyn (registered trade mark); vinyl-based resins such as an ethylene-vinyl acetate copolymer, polyvinyl chloride, and polyvinylidene chloride; acrylic resins such as an ethylene-ethyl acrylate copolymer; fluorinated carbon resins such as polytertrafluoroethylene; single films of metallic foil and the like, and laminated films thereof. It should be noted that the support has a thickness of preferably 10 μm to 500 μm, more preferably 10 μm to 200 μm.

The above-mentioned support is preferably a laminated sheet of a nonporous sheet formed of any one of the above-mentioned materials and a porous sheet. Such constitution can improve adhesion (anchoring property) between the support and the pressure-sensitive adhesive layer. In this case, the pressure-sensitive adhesive layer is preferably formed on the side of the porous sheet. The above-mentioned porous sheet is not particularly limited as long as the sheet can improve anchoring property between the support and the pressure-sensitive adhesive layer. Examples of the porous sheet include paper, a woven fabric, a nonwoven fabric, and a mechanically perforated sheet. Of those, paper, the woven fabric, or the nonwoven fabric is particularly preferred. The porous sheet preferably has a thickness of 10 μm to 500 μm. With such thickness, the anchoring property is improved, and the flexibility of the pressure-sensitive adhesive layer is excellent. In addition, when the woven fabric or the nonwoven fabric is used as the porous sheet, the porous sheet has a mass per unit area of preferably 5 g/m$^2$ to 30 g/m$^2$, more preferably 8 g/m$^2$ to 20 g/m$^2$. This is because the anchoring property can be improved. It should be noted that, when the support is the above-mentioned laminated sheet, the nonporous sheet preferably has a thickness of 1 μm to 25 μm.

Of the above-mentioned supports, a particularly suitable support is a laminated film of a polyester film (preferably a polyethylene terephthalate film) having a thickness of 1.5 μm to 6 μm and a nonwoven fabric made of a polyester (preferably a polyethylene terephthalate) having a mass per unit area of 8 g/m$^2$ to 20 g/m$^2$.

In the patch preparation of the present invention, a drug that is incorporated into the pressure-sensitive adhesive layer and can be transdermally administered is appropriately selected depending on desired purposes. Examples of such drug to be incorporated include a corticosteroid drug, a non-steroidal anti-inflammatory drug, an antirheumatic drug, a sleeping pill, an antipsychotic drug, an antidepressant, a mood stabilizer, a psychostimulant, an antianxiety drug, an antiepileptic drug, a migraine therapeutic drug, a Parkinson's disease therapeutic drug, a cerebral circulation/metabolism improver, an anti-dementia drug, an autonomic drug, a muscle relaxant, a hypotensive drug, a diuretic drug, a hypoglycemic drug, a hyperlipidemia therapeutic drug, an arthrifuge, a general anesthetic, a local anesthetic, an antibacterial drug, an antifungal drug, an antiviral drug, an anti-parasite drug, a vitamin drug, an angina pectoris therapeutic drug, a vasodilator, an antiarrhythmic drug, an antihistaminic drug, a mediator release inhibitor, a leukotriene antagonist, a female hormone drug, a thyroid hormone drug, an antithyroid drug, an antiemetic, an anti-dizziness drug, a bronchodilator, an antitussive drug, an expectorant, and a smoking cessation adjunct, which can be transdermally administered. Of those, a drug whose stability extremely reduces in a pressure-sensitive adhesive layer containing a carboxyl group can be suitably incorporated in the patch preparation of the present invention in view of the characteristics of the pressure-sensitive adhesive for forming the pressure-sensitive adhesive layer.

In the present invention, it is advantageous to use a basic drug as the drug from such a viewpoint that a patch preparation having high skin permeability is obtained. The basic drug means a drug having a basic group in its molecule. In the case of the patch preparation of the present invention containing the acrylic copolymer substantially free of a carboxyl group in the pressure-sensitive adhesive layer, for example, the inhibition of the movement of the basic drug in the pressure-sensitive adhesive layer caused by a reaction between the basic group of the basic drug and a carboxyl group can be suppressed. From such viewpoint, the basic drug is preferably a basic drug having a basic nitrogen atom, more preferably a drug having a primary, secondary, or tertiary amino group.

The content of the above-mentioned drug in the patch preparation of the present invention can be appropriately set depending on, for example, the kind of the drug and a purpose of its administration, and the age, sex, and symptom of a patient. The content of the drug in the pressure-sensitive adhesive layer is typically about 0.1 wt % to about 40 wt %, preferably about 0.5 wt % to about 30 wt %. In general, when the content is less than 0.1 wt %, the discharge of an amount of the drug effective for a treatment cannot be expected, and when the content exceeds 40 wt %, a therapeutic effect reaches its limit and an economic disadvantage arises, though a preferred content cannot be uniquely defined because the content varies depending on the selected drug.

A method of producing each of the patch and patch preparation of the present invention is not particularly limited, and an approach conventionally employed in the field can be employed. Next, specific description is given by taking a transdermal absorption tape preparation as an embodiment of the patch preparation of the present invention as an example. First, the acrylic copolymer, the organic liquid component or the like, and the drug described above are dissolved or dispersed in a solvent in the stated order. Next, a cross-linking agent is added to the above-mentioned solution or dispersion liquid as required. Thus, the composition for forming the pressure-sensitive adhesive layer is obtained. The pressure-sensitive adhesive layer is formed by applying the composition to at least one surface of the support and drying the applied composition. Further, a release liner to be described later can be laminated. Alternatively, the tape preparation can be produced by: applying the above-mentioned solution or dispersion liquid to which the cross-linking agent is added onto the release liner; drying the applied solution or dispersion liquid to form the pressure-sensitive adhesive layer on the surface of the release liner; and attaching the support onto the pressure-sensitive adhesive layer.

Examples of the above-mentioned release liner include: glassine paper, polyethylene, polypropylene, polyester, polyethylene terephthalate, polystyrene, an aluminum film, a foamed polyethylene film, and a foamed polypropylene film;

and a laminated product of two or more selected from them and products obtained by subjecting them to a silicone processing and an emboss processing. The release liner has a thickness of preferably 10 μm to 200 μm, more preferably 25 μm to 100 μm.

The above-mentioned release liner is preferably a release liner made of a polyester (especially polyethylene terephthalate) resin in terms of barrier property and a price. Further, in this case, its thickness is preferably about 25 μm to 100 μm in terms of handleability.

The application of the composition for forming the pressure-sensitive adhesive layer can be performed with any conventionally used coater such as a gravure roll coater, a reverse roll coater, a kiss-roll coater, a dip roll coater, a bar coater, a knife coater, or a spray coater. The above-mentioned composition is preferably dried under heating from the viewpoints of, for example, the acceleration of a cross-linking reaction and an improvement in production efficiency. A drying temperature is, for example, about 40° C. to about 150° C., though the drying temperature varies depending on the kind of the support to which the composition is applied.

The pressure-sensitive adhesive layer formed on at least one surface of the support in each of the patch and patch preparation of the present invention has a thickness of preferably 10 μm to 400 μm, more preferably 20 μm to 200 μm, still more preferably 30 μm to 100 μm.

In addition, after the production of the patch or the patch preparation by such method as described above, aging may be performed at a temperature equal to or more than room temperature for the purposes of: completing a cross-linking reaction; and improving anchoring property between the pressure-sensitive adhesive layer and the support. An aging temperature is preferably 25° C. to 80° C. and more preferably 40° C. to 70° C.

Next, the present invention is described in detail by way of examples, provided that the present invention is not limited to the examples.

EXAMPLE 1

Patch (1) First, 70 parts by weight of 2-ethylhexyl acrylate (which may hereinafter be referred to as "2-EHA") as the monomer (a), 10 parts by weight of N-hydroxyethylacrylamide (which may hereinafter be referred to as "HEAA") as the monomer (b), 20 parts by weight of N-vinyl-2-pyrrolidone (which may hereinafter be referred to as "N-VP") as the monomer (c), and 333.3 parts by weight of ethyl acetate as a solvent were loaded into a reaction vessel provided with a cooling tube, a nitrogen gas-introducing tube, a temperature gauge, a dropping funnel, and a stirring machine, and then the contents were stirred at room temperature for 1 hour while nitrogen gas bubbling (100 mL/min) was performed. After that, the contents in the reaction vessel were heated, and 0.2 part by weight of 2,2'-azobisisobutyronitrile (AIBN) as a polymerization initiator was added when the temperature of the contents reached 60° C. Such control that the temperature of the contents was kept at 60° C. was performed, and then polymerization was performed in a stream of a nitrogen gas for 6 hours. Next, the temperature was held at 76° C. for 15 hours. A solution of an acrylic copolymer (2-EHA/HEAA/N-VP=70/10/20) was obtained by solution polymerization based on the above-mentioned system.

(2) Isopropyl myristate (IPM) was added as an organic liquid component to the solution of the acrylic copolymer obtained in the foregoing in an amount of 42.9 parts by weight with respect to 100 parts by weight (solid content) of the acrylic copolymer. Further, a hexamethylene diisocyanate adduct of trimethylolpropane (Coronate HL) was added as an isocyanate-based cross-linking agent to the mixture in an amount of 0.5 part by weight with respect to 100 parts by weight (solid content) of the acrylic copolymer. Thus, a composition for forming a pressure-sensitive adhesive layer was prepared.

(3) The above-mentioned composition was applied to the release surface of a release liner made of a polyethylene terephthalate (PET) film having a thickness of 75 μm with an applicator, and was then dried at 100° C. for 3 minutes. Thus, the pressure-sensitive adhesive layer was formed. Next, the nonwoven fabric surface of a support was attached to the above-mentioned pressure-sensitive adhesive layer. Thus, a patch was prepared. It should be noted that a laminate of a PET film having a thickness of 2 μm and a PET nonwoven fabric having a mass per unit area of 14 g/m² was used as the support.

EXAMPLE 2

Patch

An acrylic copolymer (2-EHA/HEAA/N-VP=50/10/40) was obtained in the same manner as in Example 1 except that: 50 parts by weight of 2-ethylhexyl acrylate were used as the monomer (a); 10 parts by weight of N-hydroxyethylacrylamide were used as the monomer (b); and 40 parts by weight of N-vinyl-2-pyrrolidone were used as the monomer (c). The composition for forming the pressure-sensitive adhesive layer and then the patch were each prepared with the acrylic copolymer in the same manner as in Example 1.

COMPARATIVE EXAMPLE 1

Patch

A composition for forming a pressure-sensitive adhesive layer and then the patch were each prepared with an acrylic copolymer in the same manner as in Example 1 except that the acrylic copolymer (2-EHA/HEA/N-VP=70/10/20) was obtained by using acrylic acid hydroxyethyl ester (which may hereinafter be referred to as "HEA") instead of N-hydroxyethylacrylamide as the monomer (b) in Example 1.

COMPARATIVE EXAMPLE 2

Patch

An acrylic copolymer (2-EHA/HEAA/N-VP=50/30/20) was obtained in the same manner as in Example 1 except that: 50 parts by weight of 2-ethylhexyl acrylate were used as the monomer (a); 30 parts by weight of N-hydroxyethylacrylamide were used as the monomer (b); 20 parts by weight of N-vinyl-2-pyrrolidone were used as the monomer (c); and isopropyl alcohol was used as a solvent. A composition for forming a pressure-sensitive adhesive layer and then a patch were each prepared with the acrylic copolymer in the same manner as in Example 1 except that 0.5 part by weight of an aluminum chelate cross-linking agent (ALCH) was used as a cross-linking agent.

COMPARATIVE EXAMPLE 3

Patch

An acrylic copolymer (2-EHA/AA/N-VP=72/3/25) was obtained in the same manner as in Example 1 except that: 72 parts by weight of 2-ethylhexyl acrylate were used as the monomer (a); 3 parts by weight of acrylic acid (which may hereinafter be referred to as "AA") were used instead of the monomer (b); and 25 parts by weight of N-vinyl-2-pyrrolidone were used as the monomer (c). A composition for forming a pressure-sensitive adhesive layer and then a patch were each prepared with the acrylic copolymer in the same manner as in Example 1.

The gel fraction of the pressure-sensitive adhesive layer of each of the above-mentioned patches of Examples 1 and 2, and Comparative Examples 1 to 3 was determined. In addition, the pressure-sensitive adhesive strength, retaining strength, ball tack value, and constant-load releasing strength of each of the patches were measured, and the patch was subjected to a tube fixability test. It should be noted that the "retaining strength" was measured as an indicator for the cohesive strength of the pressure-sensitive adhesive, and the "ball tack value" was used as an indicator as to whether or not the patch hardly fell from a skin when an external load was applied to an exposed surface of the support at the beginning of the attachment of the patch to the skin. In addition, the "constant-load releasing strength" was measured as an indicator for attachment property. The above-mentioned evaluations are regarded as alternative evaluations for a fixing strength when a medical tube or the like is fixed, fixability when the patch is attached to the skin, and the like. As the results of the evaluations are better, the patch is more excellent as the patch such as a medical tape. Described below are a method of measuring the above-mentioned gel fraction, methods of measuring and evaluating the pressure-sensitive adhesive strength and the like, and a method for the tube fixability test.

<Gel Fraction>

(1) Each of the patches of the examples and the comparative examples was cut into a sample having an area of 9 cm$^2$, and then the weight ($W_1$) of its pressure-sensitive adhesive layer was measured. Next, the above-mentioned sample was attached to a tetrafluoroethylene resin (PTFE) porous film (manufactured by NITTO DENKO CORPORATION, trade name: "TEMISH"), and then the resultant was immersed in 100 mL of ethyl acetate for 72 hours.

(2) The sample was taken out of ethyl acetate and dried, and then the weight ($W_2$) of its pressure-sensitive adhesive layer was measured. Next, a gel fraction was calculated from the following equation:

Gel fraction (%)=($W_2$×100)/($W_1$×A/B)

where A represents the weight of the acrylic copolymer and the cross-linking agent, and B represents the weight of the acrylic copolymer, a plasticizer, and the cross-linking agent.

<Pressure-sensitive Adhesive Strength>

(1) The patches of the examples and the comparative examples were each cut so as to have a width of 12 mm. Thus, test pieces were produced. A clean Bakelite plate washed with a clean waste impregnated with acetone was used as an adherend.

(2) Each of the above-mentioned test pieces was lightly attached to the above-mentioned adherend, and was then attached to the above-mentioned adherend by rolling a 2-kg roller from above the test piece twice. The resultant was stored at 23° C. for 30 minutes.

(3) A releasing strength [N/12 mm] was measured under a measurement environment having a temperature of 23° C. and a relative humidity of 65% with a tensile tester under conditions of a tension speed of 300 mm/min and a releasing angle of 180°.

(4) In order for the pressure-sensitive adhesive of each test piece to be confirmed to have a sufficient cohesive strength, the presence or absence of an adhesive residue on the adherend was observed after the measurement of the releasing strength.

<Retaining Strength>

(1) A test piece was produced by cutting each of the patches of the examples and the comparative examples into a size measuring 10 mm wide by 50 mm long. A clean Bakelite plate washed with a clean waste impregnated with acetone was used as an adherend.

(2) The release liner was released from each of the above-mentioned test pieces, and then the remainder was attached to the above-mentioned adherend so as to have an adhesion area measuring 10 mm wide by 20 mm long by rolling a 2-kg roller once in a reciprocating manner. The resultant was stored at 40° C. for 20 minutes.

(3) The above-mentioned adherend was drooped under an environment having a temperature of 40° C. and a load of 300 g was applied to the free end of the above-mentioned test piece, and then the resultant was left to stand. After the application of the above-mentioned load, a time required for the test piece to fall from the adherend was measured.

<Ball Tack Value>

(1) A ball tack value was measured in conformity with Japanese Industrial Standard (JIS) Z0237, provided that, in this test, a product obtained by punching each of the patches of the examples and the comparative examples into a size measuring 50 mm wide by 50 mm long was used as a test piece for a sample convenience.

(2) The test piece was placed on a ball-rolling apparatus having a tilt angle of 30° under conditions of a temperature of 23° C. and a relative humidity of 65% so that its pressure-sensitive adhesive surface was exposed. Then, the test piece was fixed so that no step difference arose between the test piece and an entrance portion. Next, balls having different diameters were rolled on the test piece, and then the maximum diameter (ball No.) upon standstill for 5 seconds or more was defined as the ball tack value of the test piece.

<Constant-load Releasing Strength>

(1) A test piece was produced by cutting each of the patches of the examples and the comparative examples into a size measuring 12 mm wide by 70 mm long. A plate obtained by attaching a defatted, stretched collagen film on a clean Bakelite plate washed with a clean waste impregnated with acetone with a double-faced tape was used as an adherend.

(2) The release liner was released from the above-mentioned test piece, and then the remainder was attached to the above-mentioned adherend by rolling a 2-kg roller once in a reciprocating manner. One terminal of the attached test piece was released so as to have a length of 20 mm, and then a jig for suspending a load was attached to the center of the released test piece (position distant from the terminal by 10 mm). The released test piece was folded with the jig as a bend line, and then the resultant parts of the pressure-sensitive adhesive layer were attached to each other. After the resultant had been stored at 23° C. for 30 minutes, the adherend was set in a measuring apparatus so that the adherend was horizontal to the ground and the test piece was placed below the adherend. A load of 15 g was applied to the jig for suspending a load of the test piece described above. After a lapse of 1 hour from the application, a traveling distance was measured, and then a traveling speed [mm/min] was calculated.

<Tube Fixability Test>

(1) Each of the patches of the examples and the comparative examples was punched into a sample measuring 12 mm wide by 55 mm long. A rubber tube having a diameter of 5 mm, a wall thickness of 1 mm, and a length of 70 mm was bent into a U shape, and was then fixed on an upper arm portion of a volunteer panelist while one of the above-mentioned samples covered the tube so as to intersect two sites of the tube. After the fixation, a time required for the rubber tube to fall from the skin was measured.

(2) The case where the time required for the rubber tube to fall from the skin was 8 hours or more was evaluated as being ○, the case where the time was 1 hour or more and less than 8 hours was evaluated as being Δ, and the case where the time was less than 1 hour was evaluated as being x.

Table 1 shows the results of the measurements and evaluations described above.

TABLE 1

| Sample | Gel fraction (wt %) | Pressure-sensitive adhesive strength (N/12 mm) | Retaining strength (min) | Ball tack value (Ball No.) | Constant-load releasing strength (mm/min) | Tube fixability Evaluation |
|---|---|---|---|---|---|---|
| Example 1 | 90.5 | 1.04 | >12 h | 13 | 0.11 | ○ |
| Example 2 | 90.0 | 2.07 | >12 h | 11 | 0.05 | ○ |
| Comparative Example 1 | 95.1 | 0.72 | 99.5 | 10 | 3.34 | x |
| Comparative Example 2 | 9.2 | 0.51 | >12 h | No balls stopped | Not attachable to the adherend | x |
| Comparative Example 3 | 74.9 | 1.20 | >12 h | 16 | 0.06 | ○ |

As shown in Table 1, the patches of Example 1 and Example 2 containing, in its pressure-sensitive adhesive layer, the acrylic copolymer obtained from the monomer components containing specific amounts of 2-EHA and HEAA had a high pressure-sensitive adhesive strength, a high retaining strength, and a high ball tack value, and was excellent in constant-load releasing strength and tube fixability as compared with the patch of Comparative Example 1 containing, in its pressure-sensitive adhesive layer, the acrylic copolymer obtained from the monomer components containing HEA instead of HEAA or the patch of Comparative Example 2 containing, in its pressure-sensitive adhesive layer, the acrylic copolymer obtained from the monomer components containing a large amount of HEAA. Those characteristics were close to those of the patch of Comparative Example 3 containing, in its pressure-sensitive adhesive layer, the acrylic copolymer obtained from the monomer components containing 3 parts by weight of AA.

EXAMPLE 3

Patch Preparation (1) Pramipexole as a drug was added to the solution of the acrylic copolymer used in the preparation of the patch of Example 1 in an amount of 5.3 parts by weight with respect to 100 parts by weight (solid content) of the acrylic copolymer. Further, isopropyl palmitate (IPP) was added as an organic liquid component to the mixture in an amount of 72.7 parts by weight with respect to 100 parts by weight (solid content) of the acrylic copolymer. Thus, a composition for forming a pressure-sensitive adhesive layer was prepared. It should be noted that pramipexole has one primary amino group and one secondary amino group in its molecule as shown in the following formula (III).

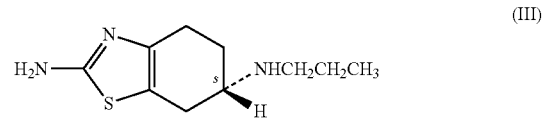

(III)

(2) The above-mentioned composition for forming a pressure-sensitive adhesive layer was applied to the release surface of a release liner made of a polyethylene terephthalate (PET) film having a thickness of 75 μm with an applicator, and was then dried at 80° C. for 5 minutes. After that, a PET film having a thickness of 25 μm as a support was attached to the resultant. Thus, a patch preparation was prepared (non-cross-linked).

COMPARATIVE EXAMPLE 4

Patch Preparation (1) Under an inert gas atmosphere, 72 parts by weight of 2-ethylhexyl acrylate, 25 parts by weight of N-vinyl-2-pyrrolidone, 3 parts by weight of acrylic acid, and 0.2 part by weight of azobisisobutyronitrile were added to ethyl acetate, and then the contents were mixed. The mixture was subjected to solution polymerization at 60° C. Thus, a solution (solid content: 28 w t %) of an acrylic copolymer (2-EHA/AA/N-VP=72/3/25) was obtained.

(2) As in Example 3, a patch preparation containing pramipexole as a drug was prepared with the above-mentioned solution of the acrylic copolymer (non-cross-linked).

<Evaluation for Drug Permeability>

Each of the patch preparations of Example 3 and Comparative Example 4 was evaluated for their drug permeability. That is, a skin extirpated from a hairless mouse was mounted on a vertical diffusion cell, each of the above-mentioned patch preparations was applied to a donor cell, and a physiological saline was applied to a receiver cell. A part of a receiver liquid was recovered at a predetermined time interval, and then the amount of pramipexole that had permeated was determined by high performance liquid chromatography (HPLC). HPLC was performed under the following conditions.

| (HPLC measurement conditions) | |
|---|---|
| Column: | TSK-gel ODS-80Ts QA (5 μm, 150 × 4.6 mm I.D.; TOSOH) |

-continued

| (HPLC measurement conditions) | |
|---|---|
| Mobile phase: | A 1% aqueous solution of triethylamine (having a pH of 7.0)/methanol (80:20) |
| Column temperature: | 40° C. |
| Flow rate: | 0.7 mL/min |
| Detector: | A UV absorptiometer (having a measurement wavelength of 262 nm) |

FIG. 1 illustrates the results of the evaluation for drug permeability. As is apparent from FIG. 1, pramipexole was observed to permeate the skin sufficiently in the patch preparation of Example 3. In contrast, in the patch preparation of Comparative Example 4 containing, in its pressure-sensitive adhesive layer, the acrylic copolymer obtained from the monomer components containing 3 parts by weight of AA, the skin permeability of pramipexole was poor and a cumulative permeation amount after 48 hours was about one half of that in the case of the patch preparation of Example 3.

As described above, the present invention provides the following patch and patch preparation. That is, each of the patch and the patch preparation has a sufficient cohesive strength, causes no adhesive residue at the time of release, shows good adhesion for a skin and a small stimulus to the skin, and has a soft feeling of attachment. In addition, when a drug or the like is incorporated, its denaturation or the like can be suppressed. Therefore, each of the patch and patch preparation of the present invention is particularly suitable for the purposes of, for example, protecting the skin and transdermally administering the drug.

Many other modifications will be apparent to and be readily practiced by those skilled in the art without departing from the scope and spirit of the invention. It should therefore be understood that the scope of the appended claims is not intended to be limited by the details of the description but should rather be broadly construed.

What is claimed is:

1. A patch preparation comprising:
   a support; and
   a pressure-sensitive adhesive layer on at least one surface of the support,
   wherein the pressure-sensitive adhesive layer comprises a drug that is transdermally administerable and an acrylic copolymer obtained by a method comprising copolymerizing monomer components comprising at least one (meth)acrylic acid alkyl ester monomer, at least one N-hydroxyalkyl(meth)acrylamide monomer, and at least one of a vinyl ether monomer and a vinyl-based monomer, said vinyl-based monomer having a heterocycle comprising a nitrogen atom,
   the (meth)acrylic acid alkyl ester monomer is included in an amount of 50 wt % to 90 wt % with respect to a total amount of the monomer components,
   the N-hydroxyalkyl(meth)acrylamide monomer is included in an amount of 1 wt % to 20 wt % with respect to the total amount of the monomer components,
   the monomer components are substantially free of a monomer having a carboxyl group,
   the (meth)acrylic acid alkyl ester monomer is at least one monomer selected from the group consisting of butyl acrylate, butyl methacrylate, 2-ethylhexyl acrylate, 2-ethylhexyl methacrylate, cyclohexyl acrylate, and cyclohexyl methacrylate, and
   the at least one of a vinyl ether monomer and a vinyl-based monomer is at least one monomer selected from the group consisting of methyl vinyl ether, ethyl vinyl ether, N-vinyl-2-pyrrolidone, 1-vinyl caprolactam, 2-vinyl-2-piperidone, and 1-vinylimidazole.

2. A patch preparation according to claim 1, wherein the vinyl-based monomer is included in an amount of 1 wt % to 40 wt % with respect to the total amount of the monomer components.

3. A patch preparation according to claim 1, wherein the pressure-sensitive adhesive layer further comprises an organic liquid component.

4. A patch preparation according to claim 1, wherein the pressure-sensitive adhesive layer is cross-linked.

5. A patch preparation according to claim 1, wherein the (meth)acrylic acid alkyl ester monomer is 2-ethylhexyl acrylate.

6. A patch preparation according to claim 1, wherein the N-hydroxyalkyl(meth)acrylamide monomer is at least one monomer selected from the group consisting of N-(2-hydroxyethyl)acrylamide, N-(2-hydroxyethyl)methacrylamide, N-(2-hydroxypropyl) acrylamide, N-(2-hydroxypropyl)methacrylamide, N-(1-hydroxypropyl) acrylamide, N-(1-hydroxypropyl)methacrylamide, N-(3-hydroxypropyl) acrylamide, N-(3-hydroxypropyl)methacrylamide, N-(2-hydroxybutyl) acrylamide, N-(2-hydroxybutyl)methacrylamide, N-(3-hydroxybutyl) acrylamide, N-(3-hydroxybutyl) methacrylamide, N-(4-hydroxybutyl) acrylamide, and N-(4-hydroxybutyl)methacrylamide.

7. A patch preparation according to claim 1, wherein the N-hydroxyalkyl(meth)acrylamide monomer is N-(2-hydroxyethyl) acrylamide.

8. A patch preparation according to claim 1, wherein the weight ratio of the (meth)acrylic acid alkyl ester monomer and the N-hydroxyalkyl (meth)acrylamide monomer in the monomer components is 99.9:0.1 to 71:29.

9. A patch preparation according to claim 1, wherein the weight ratio of the (meth)acrylic acid alkyl ester monomer and the N-hydroxyalkyl (meth)acrylamide monomer in the monomer components is 97:3 to 85:15.

10. A patch preparation according to claim 3, wherein the weight ratio of the acrylic copolymer and the organic liquid component is 1:0.1 to 2.

11. A patch preparation according to claim 3, wherein the weight ratio of the acrylic copolymer and the organic liquid component is 1:0.4 to 2.

12. A patch preparation according to claim 1, wherein the total content of the (meth)acrylic acid alkyl ester monomer and the N-hydroxyalkyl (meth) acrylamide monomer accounts for about 95 wt % of the monomer components.

* * * * *